United States Patent
Bateman et al.

(10) Patent No.: US 9,607,820 B2
(45) Date of Patent: Mar. 28, 2017

(54) ION MOBILITY SPECTROMETER WITH UPSTREAM DEVICES AT CONSTANT POTENTIAL

(75) Inventors: Robert Harold Bateman, Cheshire (GB); Kevin Giles, Cheshire (GB); Steven Derek Pringle, Darwen (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 1061 days.

(21) Appl. No.: 12/306,162

(22) PCT Filed: Jun. 25, 2007

(86) PCT No.: PCT/GB2007/002346
§ 371 (c)(1),
(2), (4) Date: Aug. 25, 2009

(87) PCT Pub. No.: WO2007/148115
PCT Pub. Date: Dec. 27, 2007

(65) Prior Publication Data
US 2010/0065733 A1    Mar. 18, 2010

Related U.S. Application Data

(60) Provisional application No. 60/830,765, filed on Jul. 14, 2006.

(30) Foreign Application Priority Data

Jun. 23, 2006  (GB) .................................. 0612503.3

(51) Int. Cl.
*H01J 49/42*  (2006.01)
*G01N 27/62*  (2006.01)
*H01J 49/00*  (2006.01)

(52) U.S. Cl.
CPC .......... *H01J 49/429* (2013.01); *G01N 27/622* (2013.01); *H01J 49/004* (2013.01); *H01J 49/0031* (2013.01)

(58) Field of Classification Search
CPC .. H01J 49/0027; H01J 49/0031; H01J 49/427; H01J 49/429; H01J 49/42
(Continued)

(56) References Cited

U.S. PATENT DOCUMENTS 4,047,030 A * 9/1977 Lobach ......................... 250/281
4,201,913 A * 5/1980 Bursack et al. ............... 250/288
(Continued)

FOREIGN PATENT DOCUMENTS

JP      2003525515       8/2003
WO    WO 00/77823      12/2000
(Continued)

*Primary Examiner* — Brooke Purinton
(74) *Attorney, Agent, or Firm* — Diederiks & Whitelaw, PLC

(57) ABSTRACT

A mass spectrometer includes an ion mobility spectrometer or separator arranged upstream of a collision or fragmentation cell. Ions are separated according to their ion mobility within the ion mobility spectrometer or separator. The kinetic energy of the ions exiting the ion mobility spectrometer or separator is increased substantially linearly with time in order to optimize the fragmentation energy of ions as they enter the collision or fragmentation cell. During the time that the potential of the ion mobility spectrometer or separator is being varied, the potential of ion-optical components upstream of the ion mobility spectrometer or separator such as an ion source, ion guide, quadrupole mass filter, optional second collision or fragmentation cell and an ion trapping device are kept constant.

17 Claims, 4 Drawing Sheets

(58) Field of Classification Search
USPC .................................. 250/281, 282, 287, 292
See application file for complete search history.

(56) References Cited

U.S. PATENT DOCUMENTS

| | | | |
|---|---|---|---|
| 5,101,105 A * | 3/1992 | Fenselau et al. ............. | 250/281 |
| 5,714,755 A * | 2/1998 | Wells et al. .................. | 250/281 |
| 6,483,109 B1 * | 11/2002 | Reinhold et al. ............. | 250/292 |
| 6,489,610 B1 * | 12/2002 | Barofsky et al. ............. | 250/287 |
| 6,534,764 B1 | 3/2003 | Verentchikov et al. | |
| 6,770,870 B2 | 8/2004 | Vestal | |
| 6,891,157 B2 * | 5/2005 | Bateman et al. ............. | 250/292 |
| 6,919,562 B1 * | 7/2005 | Whitehouse et al. ........ | 250/288 |
| 7,034,292 B1 * | 4/2006 | Whitehouse et al. ........ | 250/289 |
| 2001/0002696 A1 * | 6/2001 | Kato ............................ | 250/281 |
| 2002/0014586 A1 * | 2/2002 | Clemmer ..................... | 250/287 |
| 2002/0070338 A1 * | 6/2002 | Loboda ........................ | 250/287 |
| 2004/0041090 A1 * | 3/2004 | Bloomfield et al. .......... | 250/282 |
| 2005/0017166 A1 * | 1/2005 | Scheidemann et al. ...... | 250/288 |
| 2005/0092911 A1 * | 5/2005 | Hoyes .......................... | 250/282 |
| 2005/0242279 A1 * | 11/2005 | Verentchikov ............... | 250/287 |
| 2007/0034810 A1 * | 2/2007 | Hoyes ...................... | 250/396 R |

FOREIGN PATENT DOCUMENTS

| | | |
|---|---|---|
| WO | WO 03/091721 | 11/2003 |
| WO | 2004/109741 | 12/2004 |
| WO | 2006/030205 | 3/2006 |
| WO | 2006/048642 | 5/2006 |
| WO | 2006/061593 | 6/2006 |

\* cited by examiner

ION MOBILITY SPECTROMETER WITH UPSTREAM DEVICES AT CONSTANT POTENTIAL

CROSS REFERENCE TO RELATED APPLICATIONS

This application is the National Stage of International Application No. PCT/GB2007/002346, filed 25 Jun. 2007 and designating the United States, which claims benefit of and priority to U.S. Provisional Patent Application No. 60/830,765, filed 14 Jul. 2006, and United Kingdom Patent Application No. 0612503.3, filed 23 Jun. 2006, the entire contents of which are incorporated herein by reference.

BACKGROUND OF THE INVENTION

The present invention relates to a mass spectrometer and a method of mass spectrometry.

The majority of conventional hybrid quadrupole Time of Flight mass spectrometers comprise a quadrupole mass filter, a fragmentation cell arranged downstream of the quadrupole mass filter and a Time of Flight mass analyser arranged downstream of the fragmentation cell. The mass spectrometer is conventionally used for Data Directed Analysis (DDA) type experiments wherein a candidate parent or precursor ion is identified by interrogation of a Time of Flight (TOF) data set. Parent or precursor ions having a specific mass to charge ratio are then arranged to be selectively transmitted by the quadrupole mass filter whilst other ions are substantially attenuated by the mass filter. The selected parent or precursor ions transmitted by the quadrupole mass filter are transmitted to the fragmentation cell and are caused to fragment into fragment or daughter ions. The fragment or daughter ions are then mass analysed and mass analysis of the fragment or daughter ions yields further structural information about the parent or precursor ions.

The fragmentation of parent or precursor ions is commonly achieved by a process known as Collisional Induced Dissociation ("CID"). Ions are accelerated into the fragmentation cell and are caused to fragment upon colliding energetically with collision gas maintained within the fragmentation cell. Once sufficient fragment ion mass spectral data has been acquired, the mass filter may then be set to select different parent or precursor ions having different mass to charge ratios. The process may then be repeated multiple times. It will be appreciated that this approach can lead to an adverse reduction in the overall experimental duty cycle.

It is known to increase the experimental duty cycle by not performing the step of selecting parent or precursor ions having a specific mass to charge ratio. Instead, the known method repeatedly switches a collision or fragmentation cell back and forth between a fragmentation mode of operation and a non-fragmentation mode of operation without selecting specific parent or precursor ions.

The known approach ideally yields a first data set relating just to precursor or parent ions (in the non-fragmentation mode of operation) and a second data set relating just to fragment ions (in the fragmentation mode of operation). Individual parent or precursor ions observed in the parent ion mass spectrum may then be matched with corresponding fragment ions observed in a fragment ion mass spectrum. The known approach is essentially a parallel process unlike the previously described serial process and can result in a corresponding increase in the overall experimental duty cycle.

A problem associated with the known parallel approach is that the precursor or parent ions which are simultaneously fragmented in the fragmentation mode of operation are not specific and hence a wide range of ions having different mass to charge ratios and charge states will be attempted to be fragmented simultaneously. However, as the optimum fragmentation energy for a given parent or precursor ion is dependent both upon the mass to charge ratio of the ion to be fragmented and also the charge state of the ion, then no single fragmentation energy will exist which is optimum for all the parent or precursor ions which are desired to be fragmented simultaneously. Accordingly, some parent or precursor ions may not be fragmented in an optimal manner or indeed it is possible that some parent or precursor ions may not be fragmented at all.

It might be considered that the fragmentation energy could be progressively ramped or stepped during an acquisition period to ensure that at least some portion of the acquisition time is spent at or close to the optimum fragmentation energy for different parent or precursor ions. However, if this approach were to be adopted then a significant proportion of the acquisition time would still be spent with the parent or precursor ions possessing non-optimum fragmentation energies. As a result, the intensity of fragment ions in a fragment ion mass spectrum is likely to remain relatively low if this approach were adopted. Another consequence of attempting to step or ramp the fragmentation energy during a fragmentation mode of operation may be that some of the parent or precursor ions will remain intact and therefore, disadvantageously, these parent or precursor ions will be observed in what is supposed to be a data set relating entirely to fragment ions.

It is desired to provide an improved mass spectrometer.

SUMMARY OF THE INVENTION

According to an aspect of the present invention there is provided a mass spectrometer comprising:

an ion mobility spectrometer or separator, the ion mobility spectrometer or separator being arranged and adapted to separate ions according to their ion mobility;

one or more ion-optical devices arranged upstream of the ion mobility spectrometer or separator;

a first fragmentation, collision or reaction device arranged downstream of the ion mobility spectrometer or separator; and voltage means arranged and adapted in a first mode of operation to progressively vary and/or alter and/or scan and/or step the potential difference between the ion mobility spectrometer or separator and the first fragmentation, collision or reaction device whilst maintaining the one or more ion-optical devices at a substantially constant or unaltered potential.

The one or more ion-optical devices may comprise, for example, an ion source. The ion source may be selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

The ion source may comprise a pulsed or continuous ion source.

The one or more ion-optical devices may comprise an ion guide which may, for example, be arranged downstream of the ion source. The ion guide may comprise: (i) a multipole rod set or a segmented multipole rod set ion guide; (ii) an ion tunnel or ion funnel ion guide; or (iii) a stack or array of planar, plate or mesh electrodes forming an ion guide.

If the ion guide comprises a rod set, then the multipole rod set or the segmented multipole rod set ion guide may comprise a quadrupole rod set ion guide, a hexapole rod set ion guide, an octapole rod set ion guide or a rod set ion guide comprising more than eight rods.

If the ion guide comprises an ion tunnel or ion funnel ion guide, then the ion tunnel or ion funnel ion guide may comprise a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

If the ion guide comprises an array of electrodes, then the stack or array of planar, plate or mesh electrodes may comprise a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. Preferably, the mass spectrometer further comprises AC or RF voltage means for supplying the plurality of planar, plate or mesh electrodes with an AC or RF voltage and wherein adjacent planar, plate or mesh electrodes are supplied with opposite phases of the AC or RF voltage.

The ion guide may comprise a plurality of axial segments or at least 5, 10, 15, 20, 25, 30, 35, 40, 45, 50, 55, 60, 65, 70, 75, 80, 85, 90, 95 or 100 axial segments.

According to an embodiment transient DC voltage means may be arranged and adapted to apply one or more transient DC voltages or potentials or one or more transient DC voltage or potential waveforms to electrodes forming the ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion guide.

According to another embodiment AC or RF voltage means may be provided which are arranged and adapted to apply two or more phase-shifted AC or RF voltages to electrodes forming the ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion guide.

The ion guide preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The ion guide preferably comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the ion guide in order to confine ions radially within the ion guide. The AC or RF voltage means is preferably arranged and adapted to supply an AC or RF voltage to the plurality of electrodes of the ion guide having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) >400-450 V peak to peak; (x) 450-500 V peak to peak; and (xi) >500 V peak to peak. The AC or RF voltage means is preferably arranged and adapted to supply an AC or RF voltage to the plurality of electrodes of the ion guide having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz;

At least a portion of the ion guide is preferably maintained at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) 0.0001-0.1 mbar; and (viii) 0.001-0.01 mbar.

The one or more ion-optical devices may comprise a mass filter/analyser. The mass filter/analyser may comprise a quadrupole rod set mass filter or analyser, a Time of Flight mass filter or mass analyser, a Wein filter or a magnetic sector mass filter or mass analyser.

The one or more ion-optical devices may comprise a second fragmentation, collision or reaction device arranged upstream of the ion mobility spectrometer or separator. The second fragmentation, collision or reaction device enables parent or precursor ions to be selected and fragmented and then for the resulting first generation fragment ions to be passed to the ion mobility spectrometer or separator. The first generation fragment ions are separated according to their ion mobility in the ion mobility spectrometer or separator. The first generation fragment ions are then passed to the first fragmentation, collision or reaction device arranged downstream of the ion mobility spectrometer or separator with the result that second generation fragment ions are created in the first fragmentation, collision or reaction device.

The first fragmentation, collision or reaction device and/or the second fragmentation, collision or reaction device preferably comprises a collision or fragmentation cell arranged to fragment ions by Collisional Induced Dissociation ("CID").

The collision or fragmentation cell preferably comprises a housing having an upstream opening for allowing ions to enter the collision or fragmentation cell and a downstream opening for allowing ions to exit the collision or fragmentation cell. According to an embodiment the first fragmentation, collision or reaction device and/or the second fragmentation, collision or reaction device may comprise a multipole rod set. The first fragmentation, collision or reaction device and/or the second fragmentation, collision or reaction device may comprise a quadrupole, hexapole, octapole or higher order rod set. The multipole rod set may be axially segmented.

According to an embodiment the first fragmentation, collision or reaction device and/or the second fragmentation, collision or reaction device comprises a plurality of electrodes. The first fragmentation, collision or reaction device and/or the second fragmentation, collision or reaction device may comprise an ion tunnel or ion funnel arrangement. The first fragmentation, collision or reaction device and/or the second fragmentation, collision or reaction device may comprise at least 10, 20, 30, 40, 50, 60, 70, 80, 90 or 100 electrodes.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the electrodes of the first fragmentation, collision or reaction device and/or the second fragmentation, collision or reaction device have apertures through which ions are transmitted in use.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the electrodes of the first fragmentation, collision or reaction device and/or the second fragmentation, collision or reaction device have apertures which are of substantially the same size or area.

According to another embodiment at least 5%, 10%, 20%, 30%, 40%, 50%, 60%, 70%, 80%, 90%, 95% or 100% of the electrodes of the first fragmentation, collision or reaction device and/or the second fragmentation, collision or reaction device have apertures which become progressively larger and/or smaller in size or in area in a direction along the axis of the fragmentation, collision or reaction device.

Preferably, at least 5%, 10%, 20%, 30%, 40%, 50%, 60%, 70%, 80%, 90%, 95% or 100% of the electrodes of the first fragmentation, collision or reaction device and/or the second fragmentation, collision or reaction device have apertures having internal diameters or dimensions selected from the group consisting of: (i) $\leq 1.0$ mm; (ii) $\leq 2.0$ mm; (iii) $\leq 3.0$ mm; (iv) $\leq 4.0$ mm; (v) $\leq 5.0$ mm; (vi) $\leq 6.0$ mm; (vii) $\leq 7.0$ mm; (viii) $\leq 8.0$ mm; (ix) $\leq 9.0$ mm; (x) $\leq 10.0$ mm; and (xi) $>10.0$ mm.

The first fragmentation, collision or reaction device and/or the second fragmentation, collision or reaction device may comprise a plurality of plate or mesh electrodes and at least some of the plate or mesh electrodes may be arranged generally in the plane in which ions travel in use.

The first fragmentation, collision or reaction device and/or the second fragmentation, collision or reaction device may comprise a plurality of plate or mesh electrodes wherein at least 50%, 55%, 60%, 65%, 70%, 75%, 80%, 85%, 90%, 95% or 100% of the plate or mesh electrodes are arranged generally in the plane in which ions travel in use.

The first fragmentation, collision or reaction device and/or the second fragmentation, collision or reaction device may comprise at least 2, 3, 4, 5, 6, 7, 8, 9, 10, 11, 12, 13, 14, 15, 16, 17, 18, 19, 20 or >20 plate or mesh electrodes. The plate or mesh electrodes are preferably supplied with an AC or RF voltage. Adjacent plate or mesh electrodes are preferably supplied with opposite phases of the AC or RF voltage.

The first fragmentation, collision or reaction device and/or the second fragmentation, collision or reaction device may comprise a plurality of axial segments. The first fragmentation, collision or reaction device and/or the second fragmentation, collision or reaction device may, for example, comprise at least 5, 10, 15, 20, 25, 30, 35, 40, 45, 50, 55, 60, 65, 70, 75, 80, 85, 90, 95 or 100 axial segments.

According to an embodiment DC voltage means may be provided for maintaining a substantially constant DC voltage gradient along at least a portion of the axial length of the first fragmentation, collision or reaction device and/or the second fragmentation, collision or reaction device. The DC voltage means is preferably arranged and adapted to maintain a substantially constant DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first fragmentation, collision or reaction device and/or the second fragmentation, collision or reaction device.

According to an embodiment transient DC voltage means may be provided which are arranged and adapted to apply one or more transient DC voltages or one or more transient DC voltage waveforms to electrodes forming the first fragmentation, collision or reaction device and/or the second fragmentation, collision or reaction device in order to urge at least some ions along at least a portion of the axial length of the first fragmentation, collision or reaction device and/or the second fragmentation, collision or reaction device. The transient DC voltage means is preferably arranged and adapted to apply one or more transient DC voltages or one or more transient DC voltage waveforms to electrodes along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first fragmentation, collision or reaction device and/or the second fragmentation, collision or reaction device.

AC or RF voltage means are preferably provided which are arranged and adapted to apply one or more AC or RF voltages to electrodes forming the first fragmentation, collision or reaction device and/or the second fragmentation, collision or reaction device in order to urge at least some ions along at least a portion of the axial length of the first fragmentation, collision or reaction device and/or the second fragmentation, collision or reaction device. The AC or RF voltage means is preferably arranged and adapted to apply one or more AC or RF voltages to electrodes along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first fragmentation, collision or reaction device and/or the second fragmentation, collision or reaction device.

According to an embodiment the first fragmentation, collision or reaction device and/or the second fragmentation, collision or reaction device comprises a plurality of electrodes and the mass spectrometer further comprises AC or RF voltage means arranged and adapted to apply an AC or RF voltage to at least 1%, 5%, 10%, 20%, 30%, 40%, 50%, 60%, 70%, 80%, 90%, 95% or 100% of the plurality of electrodes of the first fragmentation, collision or reaction device and/or the second fragmentation, collision or reaction device. The AC or RF voltage means is preferably arranged and adapted to supply an AC or RF voltage to the plurality of electrodes of the first fragmentation, collision or reaction device and/or the second fragmentation, collision or reaction device having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage means is preferably arranged and adapted to supply an AC or RF voltage to the plurality of electrodes of the first fragmentation, collision or reaction device and/or the second fragmentation, collision or reaction device having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz;

The first fragmentation, collision or reaction device and/or the second fragmentation, collision or reaction device may according to a less preferred embodiment comprise a collision, fragmentation or reaction device selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

According to an embodiment the mass spectrometer further comprises means arranged and adapted to maintain at least a portion of the first fragmentation, collision or reaction device and/or the second fragmentation, collision or reaction device at a pressure selected from the group consisting of: (i) >$1.0 \times 10^{-3}$ mbar; (ii) >$1.0 \times 10^{-2}$ mbar; (iii) >$1.0 \times 10^{-1}$ mbar; (iv) >1 mbar; (v) >10 mbar; (vi) >100 mbar; (vii) >$5.0 \times 10^{-3}$ mbar; (viii) >$5.0 \times 10^{-2}$ mbar; (ix) $10^{-3}$-$10^{-2}$ mbar; and (x) $10^{-4}$-$10^{-1}$ mbar.

According to an embodiment the mass spectrometer further comprises means arranged and adapted to trap ions within the first fragmentation, collision or reaction device and/or the second fragmentation, collision or reaction device in a mode of operation.

The mass spectrometer preferably comprises a control system arranged and adapted to switch or repeatedly switch the first fragmentation, collision or reaction device and/or the second fragmentation, collision or reaction device between a first mode of operation wherein ions are substantially fragmented and a second mode of operation wherein substantially less or no ions are fragmented. In the first mode of operation ions exiting the ion mobility spectrometer or separator are preferably accelerated through a potential difference selected from the group consisting of: (i) ≥10 V; (ii) ≥20 V; (iii) ≥30 V; (iv) ≥40 V; (v) ≥50 V; (vi) ≥60 V; (vii) ≥70 V; (viii) ≥80 V; (ix) ≥90 V; and (x) ≥100 V. In the second mode of operation ions exiting the ion mobility spectrometer or separator are preferably accelerated through a potential difference selected from the group consisting of: (i) ≤20 V; (ii) ≤15 V; (iii) ≤10 V; (iv) ≤5V; and (v) ≤1V. The control system is preferably arranged and adapted to switch the first fragmentation, collision or reaction device and/or the second fragmentation, collision or reaction device between the first mode of operation and the second mode of operation at least once every 1 ms, 5 ms, 10 ms, 15 ms, 20 ms, 25 ms, 30 ms, 35 ms, 40 ms, 45 ms, 50 ms, 55 ms, 60 ms, 65 ms, 70 ms, 75 ms, 80 ms, 85 ms, 90 ms, 95 ms, 100 ms, 200 ms, 300 ms, 400 ms, 500 ms, 600 ms, 700 ms, 800 ms, 900 ms, 1 s, 2 s, 3 s, 4 s, 5 s, 6 s, 7 s, 8 s, 9 s or 10 s.

The one or more ion-optical devices may comprise an ion trap or ion trapping device which may, for example, be arranged upstream of the ion mobility spectrometer or separator.

The ion trap or ion trapping device may be arranged to pulse ions into the ion mobility spectrometer or separator. The ion trap or ion trapping device may comprise: (i) a multipole rod set or a segmented multipole rod set; (ii) an ion tunnel or ion funnel; or (iii) a stack or array of planar, plate or mesh electrodes.

If the ion trap or ion trapping device comprises a multipole rod set or a segmented multipole rod set then the ion mobility spectrometer or separator may comprise a quadrupole rod set, a hexapole rod set, an octapole rod set or a rod set comprising more than eight rods.

If the ion trap or ion trapping device comprises an ion tunnel or ion funnel then the ion tunnel or ion funnel may comprise a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

If the ion trap or ion trapping device comprises a stack or array of electrodes then the stack or array of electrodes may comprise a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use. Preferably, at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. AC or RF voltage means may be provided for supplying the plurality of planar, plate or mesh electrodes with an AC or RF voltage. Adjacent planar, plate or mesh electrodes are preferably supplied with opposite phases of the AC or RF voltage.

The ion trap or ion trapping device may further comprise AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the ion trap or ion trapping device in order to confine ions radially within the ion trap or ion trapping device. Preferably, the AC or RF voltage means is arranged and adapted to supply an AC or RF voltage to the plurality of electrodes of the ion trap or ion trapping device having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. Preferably, the AC or RF voltage means is arranged and adapted to supply an AC or RF voltage to the plurality of electrodes of the ion trap or ion trapping device having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (X) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz;

The voltage means is preferably arranged and adapted to vary and/or alter and/or scan and/or step the potential difference through which ions pass as ions pass from the ion mobility spectrometer or separator to the first fragmentation, collision or reaction device. The voltage means is preferably arranged and adapted to vary and/or alter and/or scan and/or step the potential difference through which ions pass as they pass from the ion mobility spectrometer or separator to the first fragmentation, collision or reaction device in a substantially continuous and/or linear and/or progressive and/or regular manner. According to a less preferred embodiment the voltage means may be arranged and adapted to vary and/or alter and/or scan and/or step the potential difference through which ions pass as they pass from the ion mobility spectrometer or separator to the first fragmentation, collision or reaction device in a substantially non-continuous and/or non-linear manner.

The voltage means is preferably arranged and adapted to accelerate ions emerging from the ion mobility spectrometer or separator at a time $t_1$ through a first potential difference $V_1$ and to accelerate second different ions emerging from the ion mobility spectrometer or separator at a second later time $t_2$ through a second different potential difference $V_2$.

Preferably, $V_2>V_1$. The voltage means is preferably arranged and adapted to progressively increase with time the potential difference through which ions pass as they are transmitted from the ion mobility spectrometer or separator to the first fragmentation, collision or reaction device.

According to a less preferred embodiment, $V_2<V_1$. This embodiment may be implemented, for example, when a multiple charged ion is fragmented. According to this embodiment the voltage means may be arranged and adapted to decrease with time the potential difference through which ions pass as they are transmitted from the ion mobility spectrometer or separator to the first fragmentation, collision or reaction device.

The voltage means is preferably arranged and adapted to accelerate ions such that they pass through a substantially optimum potential difference for fragmentation as they enter the first fragmentation, collision or reaction device.

The voltage means is preferably arranged and adapted to accelerate and/or decelerate ions into the first fragmentation, collision or reaction device.

The ion mobility spectrometer or separator preferably comprises a gas phase electrophoresis device.

According to an embodiment the ion mobility spectrometer or separator may comprise a drift tube and one or more electrodes for maintaining an axial DC voltage gradient along at least a portion of the drift tube. Means are preferably provided for maintaining an axial DC voltage gradient along at least a portion of the drift tube.

According to an embodiment the ion mobility spectrometer or separator may comprise one or more multipole rod sets. The ion mobility spectrometer or separator may comprise one or more quadrupole, hexapole, octapole or higher order rod sets. The one or more multipole rod sets may be axially segmented or comprise a plurality of axial segments.

The ion mobility spectrometer or separator preferably comprises a plurality of electrodes. The ion mobility spectrometer or separator preferably comprises at least 10, 20, 30, 40, 50, 60, 70, 80, 90 or 100 electrodes. At least 5%, 10%, 15%, 20%, 25%, 30%, 35%, 40%, 45%, 50%, 55%, 60%, 65%, 70%, 75%, 80%, 85%, 90%, 95% or 100% of the electrodes of the ion mobility spectrometer or separator may have apertures through which ions are transmitted in use.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the electrodes of the ion mobility spectrometer or separator have apertures which are of substantially the same size or area.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the electrodes of the ion mobility spectrometer or separator have apertures which become progressively larger and/or smaller in size or in area in a direction along the axis of the ion guide or ion trap.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes of the ion mobility spectrometer or separator have apertures having internal diameters or dimensions selected/from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The ion mobility spectrometer or separator may according to an embodiment comprise a plurality of plate or mesh electrodes wherein at least some of the plate or mesh electrodes are arranged generally in the plane in which ions travel in use.

The ion mobility spectrometer or separator may comprise a plurality of plate or mesh electrodes wherein at least 50%, 55%, 60%, 65%, 70%, 75%, 80%, 85%, 90%, 95% or 100% of the plate or mesh electrodes are arranged generally in the plane in which ions travel in use.

The ion mobility spectrometer or separator may comprise at least 2, 3, 4, 5, 6, 7, 8, 9, 10, 11, 12, 13, 14, 15, 16, 17, 18, 19, 20 or >20 plate or mesh electrodes. The plate or mesh electrodes are preferably supplied with an AC or RF voltage.

Adjacent plate or mesh electrodes are preferably supplied with opposite phases of the AC or RF voltage.

The ion mobility spectrometer or separator may comprise a plurality of axial segments. The ion mobility spectrometer or separator may comprise at least 5, 10, 15, 20, 25, 30, 35, 40, 45, 50, 55, 60, 65, 70, 75, 80, 85, 90, 95 or 100 axial segments.

According to an embodiment DC voltage means may be provided which is arranged to maintain a substantially constant DC voltage gradient along at least a portion of the axial length of the ion mobility spectrometer or separator. The DC voltage means may be arranged and adapted to maintain a substantially constant DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

According to an embodiment transient DC voltage means may be arranged and adapted to apply one or more transient DC voltages or potentials or one or more transient DC voltage or potential waveforms to electrodes forming the ion mobility spectrometer or separator in order to urge at least some ions along at least a portion of the axial length of the ion mobility spectrometer or separator.

The transient DC voltage means may be arranged and adapted to apply one or more transient DC voltages or potentials or one or more transient DC voltage or potential waveforms to electrodes along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

AC or RF voltage means may be provided which are arranged and adapted to apply one or more AC or RF voltages to electrodes forming the ion mobility spectrometer or separator in order to urge at least some ions along at least a portion of the axial length of the ion mobility spectrometer or separator.

The AC or RF voltage means is preferably arranged and adapted to apply one or more AC or RF voltages to electrodes along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The ion mobility spectrometer or separator preferably comprises a plurality of electrodes. The mass spectrometer preferably further comprises AC or RF voltage means arranged and adapted to apply an AC or RF voltage to at least 5%, 10%, 20%, 30%, 40%, 50%, 60%, 70%, 80%, 90%, 95% or 100% of the plurality of electrodes of the ion mobility spectrometer or separator in order to confine ions radially within the ion mobility spectrometer or separator.

The AC or RF voltage means is preferably arranged and adapted to supply an AC or RF voltage to the plurality of electrodes of the ion mobility spectrometer or separator having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage means is arranged and adapted to supply an AC or RF voltage to the plurality of electrodes of the ion mobility spectrometer or separator having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz;

There is preferably provided means arranged and adapted to maintain at least a portion of the ion mobility spectrometer or separator at a pressure selected from the group consisting of: (i) $>1.0\times10^{-3}$ mbar; (ii) $>1.0\times10^{-2}$ mbar; (iii) $>1.0\times10^{-1}$ mbar; (iv) >1 mbar; (v) >10 mbar; (vi) >100 mbar; (vii) $>5.0\times10^{-3}$ mbar; (viii) $>5.0\times10^{-2}$ mbar; (ix) $10^{-3}$-$10^{-2}$ mbar; and (x) $10^{-4}$-$10^{-1}$ mbar.

An ion guide or transfer means may be arranged between the ion mobility spectrometer or separator and the first fragmentation, collision or reaction device in order to guide or transfer ions emerging from the ion mobility spectrometer or separator to or into the first fragmentation, collision or reaction device.

A mass analyser is preferably arranged downstream of the first fragmentation, collision or reaction device and/or the second fragmentation, collision or reaction device. The mass analyser is preferably selected from the group consisting of: (i) a Fourier Transform ("FT") mass analyser; (ii) a Fourier Transform Ion Cyclotron Resonance ("FTICR") mass analyser; (iii) a Time of Flight ("TOF") mass analyser; (iv) an orthogonal acceleration Time of Flight ("oaTOF") mass analyser; (v) an axial acceleration Time of Flight mass analyser; (vi) a magnetic sector mass spectrometer; (vii) a Paul or 3D quadrupole mass analyser; (viii) a 2D or linear quadrupole mass analyser; (ix) a Penning trap mass analyser; (x) an ion trap mass analyser; (xi) a Fourier Transform orbitrap; (xii) an electrostatic Ion Cyclotron Resonance mass spectrometer; (xiii) an electrostatic Fourier Transform mass spectrometer; and (xiv) a quadrupole mass analyser.

According to an aspect of the present invention there is provided a method of mass spectrometry comprising:

separating ions according to their ion mobility in an ion mobility spectrometer or separator;

providing one or more ion-optical devices upstream of the ion mobility spectrometer or separator;

providing a first fragmentation, collision or reaction device downstream of the ion mobility spectrometer or separator;

progressively varying and/or altering and/or scanning and/or stepping the potential difference between the ion mobility spectrometer or separator and the first fragmentation, collision or reaction device whilst maintaining the one or more ion-optical devices at a substantially constant or unaltered potential.

The preferred embodiment preferably involves temporally separating ions in a substantially predictable manner using an ion mobility spectrometer or separator device which is preferably arranged upstream of a fragmentation device. The fragmentation device preferably comprises a collision or fragmentation cell containing a collision gas maintained at a pressure $>10^{-3}$ mbar. At any given time the mass to charge ratio range (for a given charge state) of ions exiting the ion mobility spectrometer or separator can generally be predicted. Accordingly, the mass to charge ratio of ions which are received by the collision or fragmentation cell at any particular time can also be generally predicted. The preferred embodiment involves setting or controlling the energy of the ions entering the collision or fragmentation cell and varying the energy with time in such a way that substantially all parent or precursor ions are arranged to possess substantially optimal energy for fragmentation as they are preferably accelerated into or towards the fragmentation device from the ion mobility spectrometer or separator device.

The preferred embodiment enables ions to be fragmented with a substantially improved fragmentation efficiency across the entire mass to charge ratio range of ions of interest and therefore represents an important advance in the art.

A particularly important aspect of the preferred embodiment is that the potential of ion-optical devices arranged upstream of the ion mobility spectrometer or separator is preferably left substantially constant or unaltered whilst the potential difference between the ion mobility spectrometer or separator and the first fragmentation, collision or reaction device is preferably progressively increased.

Conventionally, if the potential difference between a first ion-optical device and a second ion-optical device arranged downstream of the first ion-optical device in a mass spectrometer were to be progressively increased then the potential of all other ion-optical devices upstream of the first ion-optical device would also be increased in tandem with increasing the potential of the first ion-optical device relative to the second ion-optical device.

According to the preferred embodiment ion-optical devices such as an ion source, an ion guide, a quadrupole rod set mass filter, a second optional fragmentation, collision or reaction device and a trapping device or ion trap may all be provided or arranged upstream of the ion mobility spectrometer or separator. According to the preferred embodiment instead of varying or increasing the potential of each of these ion-optical devices in tandem with increasing the potential of the ion mobility spectrometer or separator, the potential of these ion-optical devices is preferably substantially unaltered during the time period that the potential difference between the ion mobility spectrometer or separator and the first fragmentation, collision dr reaction device is being varied.

According to the preferred embodiment at the end of the time period during which the potential difference between the ion mobility spectrometer or separator and the first fragmentation, collision or reaction device is varied or increased, the potential of the ion mobility spectrometer or separator can then be lowered and/or returned to the potential which it was at the beginning of the time period. A new pulse of ions can then be admitted into the ion mobility spectrometer or separator. Ions are preferably pulsed into the ion mobility spectrometer or separator by being pulsed out of an ion trap or ion trapping device which is preferably arranged upstream of the ion mobility spectrometer or separator. The present inventors have realised that the cyclic nature of the preferred mode of operation enables the potentials at which the ion-optical devices arranged upstream of the ion mobility spectrometer or separator are maintained to be decoupled from the potential at which the ion mobility spectrometer or separator is maintained during use. Increasing only the potential of the ion mobility spectrometer or separator relative to the first fragmentation, collision or reaction device whilst maintaining ion-optical devices upstream of the ion mobility spectrometer or separator at a substantially constant potential is a significant advantage and considerably simplifies the preferred mode of operation of the mass spectrometer.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENTS

Figure 1:
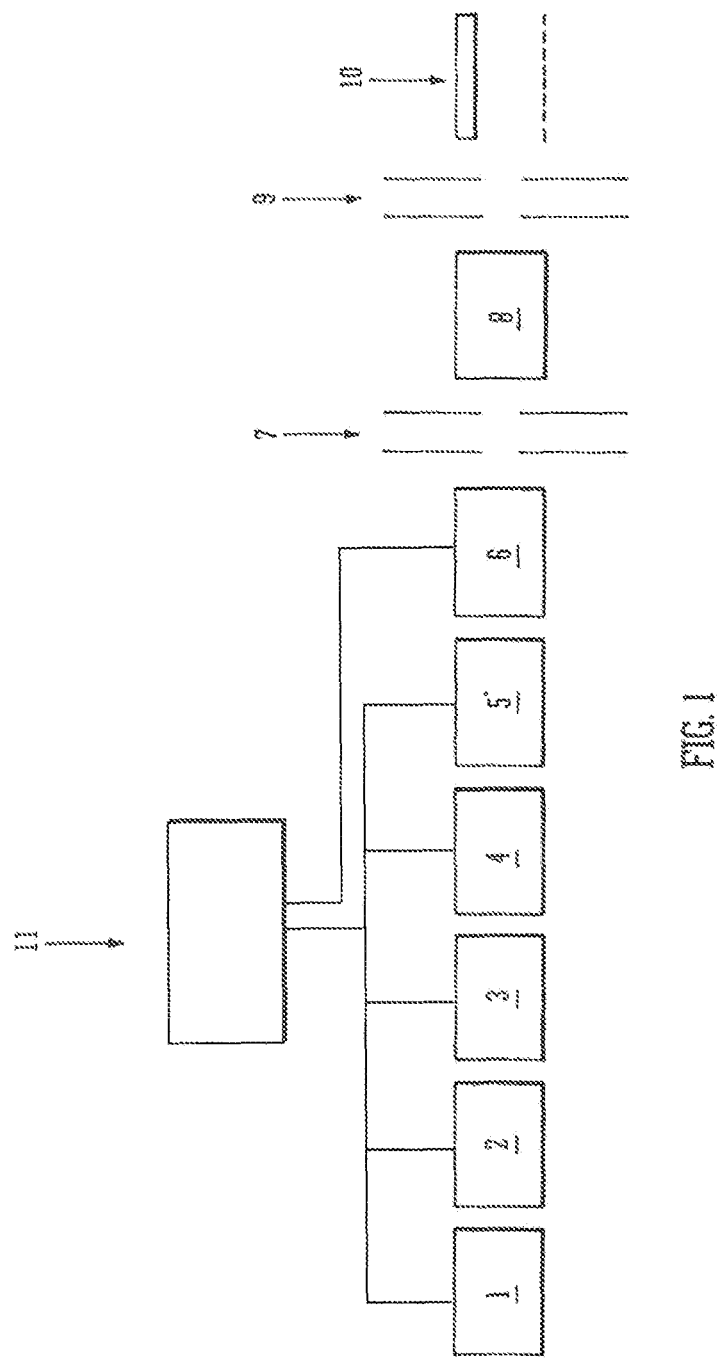
FIG. 1 shows in schematic form a mass spectrometer according to a preferred embodiment of the present invention.

A preferred embodiment of the present invention will now be described with reference to FIG. 1. A mass spectrometer according to the preferred embodiment of the present invention preferably comprises an ion source 1. An ion guide 2 is preferably arranged downstream of the ion source 1. The ion guide 2 may according to an embodiment comprise a quadrupole rod set ion guide or an ion tunnel ion guide comprising a plurality of electrodes having apertures through which ions are transmitted in use. One or more transient DC voltage waveforms may be applied to the electrodes of the ion guide 2 in order to urge ions long the length of the ion guide 2.

Downstream of, the ion guide 2 a mass filter 3 is preferably provided. The mass filter 3 preferably comprises a quadrupole rod set mass filter 3. Downstream of the mass filter 3 an optional collision, fragmentation or reaction device 4 may be provided.

As will be discussed in more detail below, the optional collision, fragmentation or reaction device 4 if provided enables $MS^2$ experiments to be performed wherein specific parent or precursor ions can be selected by the mass filter 3. The parent or precursor ions which are then onwardly transmitted by the mass filter 3 are then preferably passed to the collision, fragmentation or reaction device 4. The parent or precursor ions are then preferably fragmented producing a plurality of first generation fragment ions. The first generation fragment ions are then preferably pulsed into an ion mobility spectrometer or separator 6. The first generation fragment ions are then preferably temporally separated according to their ion mobility as they pass through the ion mobility spectrometer or separator 6. The first generation fragment ions are then preferably accelerated through an optimal potential difference such that they are then subsequently themselves fragmented to produce second generation fragment ions as they pas through a transfer optic 7 or ion guide and then a further collision, fragmentation or reaction device 8 arranged downstream of the ion mobility spectrometer or separator 6.

An ion trap or ion trapping device 5 is preferably provided downstream of the mass filter 3 and the optional collision, fragmentation or reaction device 4. The ion trap or ion trapping device 5 is upstream of the ion mobility spectrometer or separator 6.

The ion mobility spectrometer or separator 6 is preferably arranged to separate ions according to their ion mobility or a related physico-chemical property. The ion mobility spectrometer or separator 6 preferably comprises a form of gas phase electrophoresis device.

The ion mobility spectrometer or separator 6 may take a number of different forms which will be discussed in more detail below. According to an embodiment the ion mobility spectrometer or separator 6 may comprise a travelling wave ion mobility separator device wherein one or more travelling or transient DC voltages or potentials or DC voltage or potential waveforms are applied to a plurality of electrodes forming the device 6. Alternatively, the device 6 may comprise a drift cell wherein ions may or may not be confined radially.

According to one embodiment the ion mobility spectrometer or separator 6 may comprise a drift tube having one or more guard ring electrodes. A constant axial DC voltage gradient may be maintained along the length of the drift tube. The drift tube is preferably maintained at a gas pressure $>10^{-3}$ mbar, more preferably $>10^{-2}$ mbar and ions are preferably urged along and through the device by the application of the constant DC voltage gradient. Ions having a relatively high ion mobility will preferably emerge from the ion mobility spectrometer or separator 6 prior to ions having a relatively low ion mobility.

According to other embodiments the ion mobility spectrometer or separator 6 may comprises a multipole rod set. According to a particularly preferred embodiment the multipole rod set (for example, a quadrupole rod set) may be axially segmented. The plurality of axial segments may be maintained at different DC potentials so that a static axial DC voltage gradient is maintained along the length of the ion mobility spectrometer or separator 6. It is also contemplated that according to another embodiment one or more time varying DC potentials may be applied to the axial segments in order to urge ions along and through the axial length of the ion mobility spectrometer or separator 6. Alternatively, one or more AC or RF voltages may be applied to the axial segments in order to urge ions along the length of the ion mobility spectrometer or separator 6. It will be appreciated that according to these various embodiments ions are caused to separate according to their ion mobility as they pass through a background gas present in the axial drift region of the ion mobility spectrometer or separator 6.

The ion mobility spectrometer or separator 6 may according to another embodiment comprise an ion tunnel or ion funnel arrangement comprising a plurality of plate, ring or wire electrodes having apertures through which ions are transmitted in use. In an ion tunnel arrangement substantially all of the electrodes have similar sized apertures. In an ion funnel arrangement the size of the apertures preferably becomes progressively smaller or larger. According to these embodiments a constant DC voltage gradient may be maintained along the length of the ion tunnel or ion funnel ion mobility spectrometer or separator. Alternatively, one or more transient or time varying DC potentials or a multi-phase AC or RF voltage may be applied to the electrodes forming the ion tunnel or ion funnel arrangement in order to urge ions along the length of the ion mobility spectrometer or separator 6.

According to a yet further embodiment the ion mobility spectrometer or separator 6 may comprise a sandwich plate arrangement comprising a plurality of plate or mesh electrodes arranged generally in the plane in which ions travel in use. The electrode arrangement may also preferably be axially segmented so that as with the other embodiments either a static DC potential gradient, a time varying DC potential or a multi-phase AC or RF voltage may be applied to the axial segments in order to urge ions along and through the length of the ion mobility spectrometer or separator 6.

Ions are preferably radially confined within the ion mobility spectrometer or separator 6 due to the application of an AC or RF voltage to the electrodes forming the ion mobility spectrometer or separator 6. The applied AC or RF voltage preferably results in a radial pseudo-potential well being created which preferably prevents ions escaping from the ion mobility spectrometer or separator 6 in the radial direction.

The ion trap 5 preferably provided upstream of the ion mobility spectrometer or separator 6 is preferably arranged to periodically release one or more pulses of ions into or towards the ion mobility spectrometer or separator 6.

A transfer optic 7 or ion guide is preferably arranged downstream of the ion mobility spectrometer or separator 6 in order to receive ions emitted or leaving the ion mobility spectrometer or separator 6. The transfer optic 7 or ion guide may according to one embodiment comprise a quadrupole rod set ion guide or an ion tunnel ion guide comprising a plurality of electrodes having apertures through which ions are transmitted in use.

A fragmentation, collision or reaction device 8 which preferably comprises a collision or fragmentation cell 8 is preferably arranged downstream of the transfer optic 7 or ion guide. The fragmentation, collision or reaction device 8 may, according to an alternative embodiment be arranged to receive ions emitted directly or indirectly from the ion mobility spectrometer or separator 6.

The fragmentation, collision or reaction device 8 preferably comprises a collision or fragmentation cell 8 which may take a number of different forms. In the simplest form the fragmentation, collision or reaction device 8 may comprise a multipole rod set collision or fragmentation cell. According to an embodiment the collision or fragmentation cell 8 may comprise a travelling wave collision or fragmentation cell 8 wherein one or more travelling or transient DC voltages or potentials or transient DC voltage or potential waveforms are preferably applied to the electrodes forming the collision or, fragmentation cell 8 in order to urge ions along the length of the collision or fragmentation cell 8. The application of a transient DC potential or voltage to the electrodes forming the fragmentation, collision or reaction device 8 preferably speeds up the transit time of fragment ions through the collision or fragmentation cell 8.

Alternatively, the collision or fragmentation cell 8 may comprise a linear acceleration collision or fragmentation cell wherein a constant axial DC voltage gradient is maintained along at least a portion of the axial length of the collision or fragmentation cell 8.

According to the preferred embodiment the collision or fragmentation cell 8 is preferably arranged to fragment ions by Collisional Induced Dissociation ("CID") wherein ions are accelerated into the collision or fragmentation cell 8 with sufficient energy such that the ions fragment upon colliding with gas molecules present within the collision or fragmentation cell 8. According to a less preferred embodiment the fragmentation, collision or reaction device 8 may comprise a device for fragmenting ions by Surface Induced Dissociation ("SID") wherein ions are fragmented by accelerating the ions onto a surface or electrode which then causes the ions to fragment. According to other less preferred embodiments it is contemplated that the fragmentation, collision or reaction device 8 may take other forms.

According to an embodiment the fragmentation, collision or reaction device 8 may comprise a multipole rod set. According to an embodiment the multipole rod set (for example, a quadrupole rod set) may be axially segmented. The plurality of axial segments may be maintained at different DC potentials so that a static axial DC voltage gradient is preferably maintained along at least a portion of the length of the fragmentation, collision or reaction device 8. It is contemplated that according to another embodiment one or more time varying DC voltages or potentials or one or more transient DC voltage or potential waveforms may be applied to the axial segments of the fragmentation, collision or reaction device 8 in order to urge fragment ions along and through the axial length of the fragmentation, collision or reaction device 8. Alternatively, one or more multi-phase AC or RF voltages may be applied to the axial segments in order to urge fragment ions along the length of the fragmentation, collision or reaction device 8.

Although it is not necessary to apply a constant non-zero DC voltage gradient along the length of the fragmentation, collision or reaction device 8 nor to apply one or more transient DC or multi-phase AC or RF voltages to the electrodes forming the fragmentation, collision or reaction device 8, the application of a static or time varying electric field along the length of the fragmentation, collision or reaction device 8 can improve the transit time of fragment ions through the fragmentation, collision or reaction device 8.

The fragmentation, collision or reaction device 8 may according to another embodiment comprise an ion tunnel or ion funnel arrangement comprising a plurality of plate electrodes having apertures through which ions are transmitted in use. In an ion tunnel arrangement substantially all of the electrodes have similar sized apertures. In an ion funnel arrangement the size of the apertures preferably becomes progressively smaller or larger. According to these embodiments a constant DC voltage gradient may be maintained along the length of the ion tunnel or ion funnel fragmentation, collision or reaction device 8. Alternatively, one or more transient or time varying DC voltages potentials, transient DC voltage or potential waveforms or a multi-phase AC or RF voltage may be applied to the electrodes forming the ion tunnel or ion funnel arrangement in order to urge ions along the length of the fragmentation, collision or reaction device 8.

According to a yet further embodiment the fragmentation, collision or reaction device 8 may comprise a sandwich plate arrangement wherein the fragmentation, collision or reaction device 8 comprises a plurality of plate or mesh electrodes arranged generally in the plane in which ions travel in use. The electrode arrangement may also preferably be axially segmented so that as with other embodiments either a static DC potential gradient, a time varying DC potential or a multi-phase AC or RF voltage may be applied to the axial segments in order to urge fragment ions along and through the fragmentation, collision or reaction device 8.

Ions are preferably radially confined within the fragmentation, collision or reaction device 8 due to the application of an AC or RF voltage to the electrodes forming the fragmentation, collision or reaction device 8. The applied AC or RF voltage preferably results in a radial pseudo-potential well being created which preferably prevents ions from escaping from the fragmentation, collision or reaction device 8 in the radial direction.

A collision or fragmentation gas is preferably provided within the fragmentation, collision or reaction device 8. The collision or fragmentation gas may comprise helium, methane, neon, nitrogen, argon, xenon, air or a mixture of such gases. Nitrogen or argon are particularly preferred.

A further transfer optic 9 or ion guide may be arranged downstream of the fragmentation, collision or reaction device 8 to act as an interface between the fragmentation, collision or reaction device 8 and a mass analyser such as an orthogonal acceleration Time of Flight mass analyser. The further transfer optic 9 or ion guide may according to an embodiment comprise a quadrupole rod set ion guide or an ion tunnel ion guide comprising a plurality of electrodes having apertures through which ions are transmitted in use. A pusher electrode 10 of an orthogonal acceleration Time of Flight mass analyser is shown in FIG. 1. The drift region, reflection and ion detector of the orthogonal acceleration mass analyser are not shown in FIG. 1. The operation of a Time of Flight mass analyser is well known to those skilled in the art and will not therefore be described in more detail.

The ion source 1 may take a number of different forms. According to a particularly preferred embodiment the ion source 1 may comprise a Matrix Assisted Laser Desorption Ionsiation ("MALDI") ion source. A MALDI ion source is particularly advantageous in that ions produced by the MALDI ion source 1 will normally be predominantly singly charged. This simplifies the operation of the ion mobility spectrometer or separator 6 and in particular simplifies the step of varying the potential difference between the ion mobility spectrometer or separator 6 and the fragmentation, collision or reaction device 8 which ions are caused to experience as they exit the ion mobility spectrometer or separator 6. This aspect of the preferred embodiment will be described in more detail below.

According to other embodiments other types of ion source 1 may be used. For example, an Atmospheric Pressure Ionisation (API) ion source and particularly an Electrospray ionisation ion source may be used.

Ions emitted by the ion source 1 may be accumulated for a period of time either within the ion source 1 itself, or within the ion trap or ion trapping device 5 or within an upstream portion or section of the ion mobility spectrometer or separator 6. For example, the ion mobility spectrometer or separator 6 may comprise an upstream portion which acts as an ion trapping region and also comprise a downstream portion in which ions are separated according to their ion mobility. After ions have been accumulated in some manner, a packet or pulse of ions having a range of different mass to charge ratios is then preferably released. The packet or pulse of ions is preferably arranged to be transmitted or passed either to the ion mobility spectrometer or separator 6 or to the main section of the ion mobility spectrometer or separator 6 in which ions are separated according to their ion mobility.

Since ions emitted from a MALDI ion source are predominantly singly charged, then the time taken by ions to pass through and hence exit the ion mobility spectrometer or separator 6 will preferably be a function of the mass to charge ratio of the ions. The relationship between the mass to charge ratio of an ion and the transit or exit time through or from an ion mobility spectrometer or separator 6 is generally known and predictable and will be discussed in more detail with reference to FIG. 2.

Figure 2:
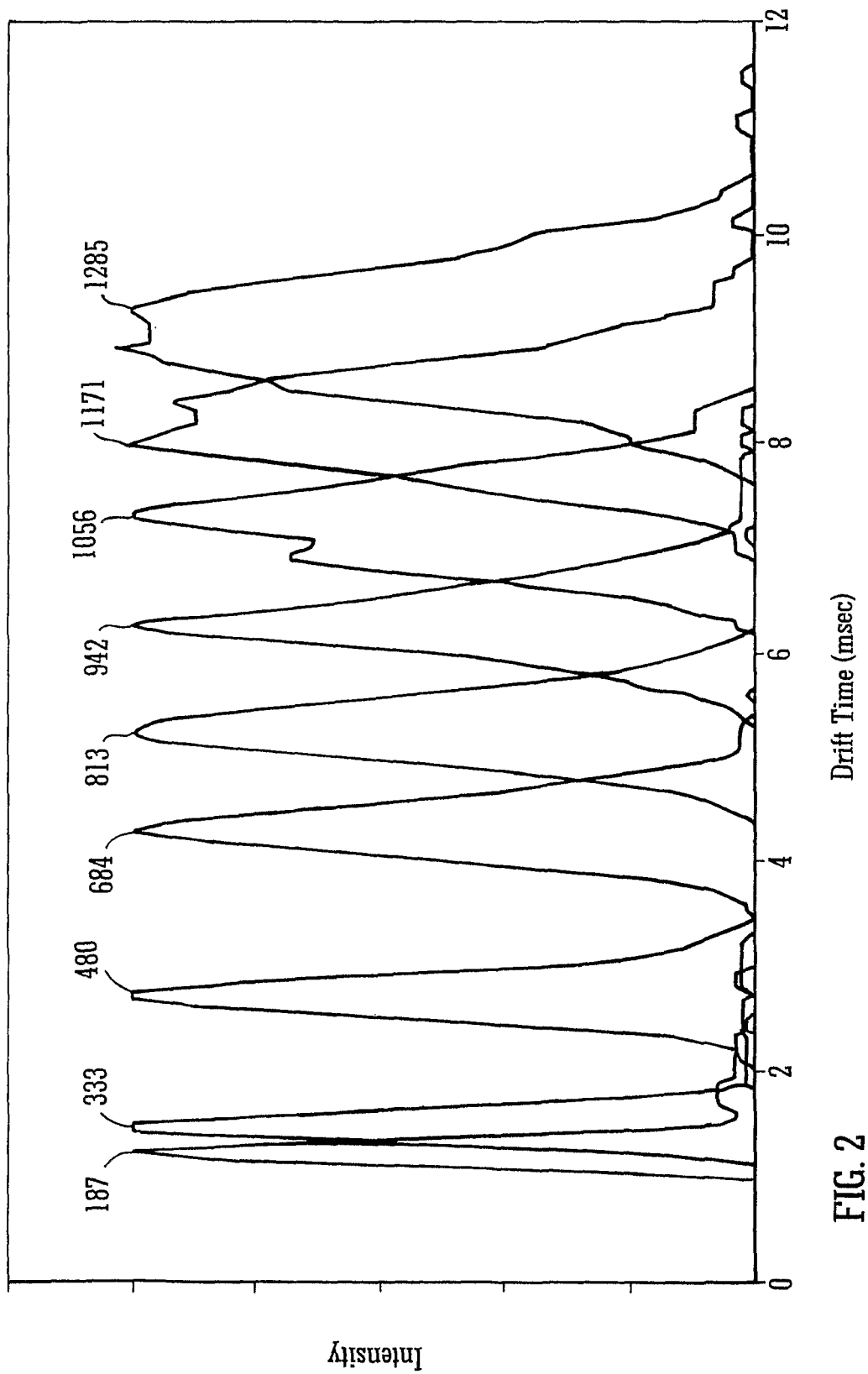
FIG. 2 shows the time taken for singly charged ions having different mass to charge ratios to exit an ion mobility spectrometer or separator according to a preferred embodiment.

FIG. 2 shows some experimental results which show peaks representing different singly charged ions and their corresponding mass to charge ratio and the time taken for the ions to pass through and exit an ion mobility spectrometer or separator 6 according to the preferred embodiment. As can be seen from FIG. 2, singly charged ions having relatively low mass to charge ratios pass through and exit the ion-mobility spectrometer or separator 6 relatively quickly whereas singly charged ions having relatively high mass to charge ratios take substantially longer to pass through and exit the ion mobility spectrometer or separator 6. For example, as can be seen from FIG. 2, ions having a mass to charge ratio <350 will transit the length of the ion mobility spectrometer or separator 6 in less than 2 ms whereas ions having a mass to charge ratio >1000 will take approximately at least 7 ms to transit the length of the ion mobility spectrometer or separator 6.

In FIG. 2 the time shown as zero corresponds with the time that an ion packet or pulse is first released from an accumulation stage or ion trapping region into the main body of the ion mobility spectrometer or separator 6. It can be seen from FIG. 2 that with the particular ion mobility spectrometer or separator 6 used, the highest mass to charge, ratio ions can take up to about 12 ms or longer to exit the ion mobility spectrometer or separator 6.

The fragmentation, collision or reaction device 8 may be arranged to be operated in a constant fragmentation mode of operation. However, according to other embodiments the fragmentation, collision or reaction device 8 may be effectively repeatedly switched ON and OFF during the course of an experimental run or acquisition. When the fragmentation, collision or reaction device 8 is operated in a non-fragmentation (i.e. parent ion) mode of operation then the fragmentation, collision or reaction device 8 is effectively switched OFF and the fragmentation, collision or reaction device 8 then effectively acts as an ion guide. In this mode of operation the potential difference maintained between the ion mobility spectrometer or separator 6 and the fragmentation, collision or reaction device 8 is preferably relatively low. Ions exiting the ion mobility spectrometer or separator 6 are not therefore accelerated into the fragmentation, collision or reaction device 8 with sufficient energy such that they are caused to fragment. Accordingly, there is minimal or substantially no fragmentation of parent or precursor ions as they pass through the fragmentation, collision or reaction device 8 in this mode of operation. The parent or precursor ions preferably pass through and exit the fragmentation, collision or reaction device 8 substantially unfragmented. The parent or precursor ions which emerge substantially unfragmented from the fragmentation, collision or reaction device 8 then preferably pass through the further transfer optic or ion guide 9 and are then preferably mass analysed by, for example, an orthogonal acceleration Time of Flight mass analyser 10. A parent or precursor ion mass spectrum may then be obtained.

When the fragmentation, collision or reaction device 8 is operated in a fragmentation mode of operation then the potential difference maintained between the ion mobility spectrometer or separator 6 and the fragmentation, collision or reaction device 8 is preferably set such that ions emerging from the ion mobility spectrometer or separator 6 are caused to enter the fragmentation, collision or reaction device 8 with optimal energy for fragmentation. According to the preferred embodiment, the potential difference maintained between the exit of the ion mobility spectrometer or separator 6 and the entrance to the fragmentation, collision or reaction device 8 is preferably progressively increased with time whilst the fragmentation, collision or reaction device 8 is being operated in a fragmentation mode of operation (i.e. before it is switched, for example, back to a non-fragmentation mode of operation). This ensures that the ions which emerge from the ion mobility spectrometer or separator 6 are accelerated to an energy such that they then enter the fragmentation, collision or reaction device 8 with the optimum energy for fragmentation. During the time that the potential of the ion mobility spectrometer or separator 6 is being varied, the potential of ion-optical components upstream of the ion mobility spectrometer or separator 6, such as an ion source 1, ion guide 2, quadrupole mass filter 3, optional second collision or fragmentation cell 4 and an ion trapping device 5, are kept constant by a voltage source or means 11.

It is contemplated that according to an embodiment the fragmentation, collision or reaction device 8 may spend unequal amounts of time in a non-fragmentation mode of operation as compared with in a fragmentation mode of operation. For example, during an experimental run or acquisition the fragmentation, collision or reaction device 8 may spend comparatively longer in a fragmentation mode of operation than in a non-fragmentation mode of operation.

Figure 3:
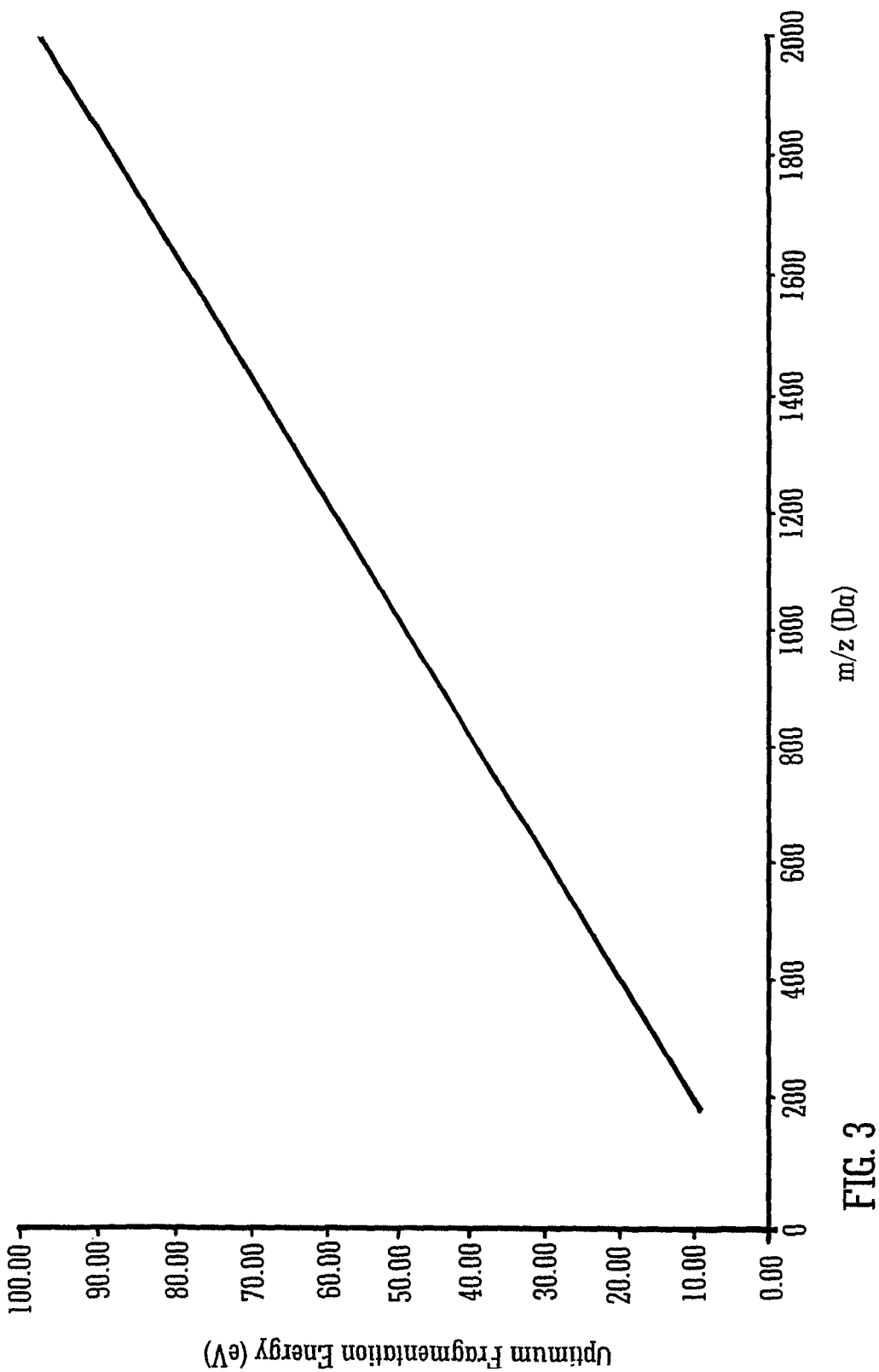
FIG. 3 shows a plot of optimum fragmentation energy against mass to charge ratio for singly charged ions as emitted, for example, from a MALDI ion source.

The optimum fragmentation energy in eV for singly charged ions emitted, for example, from a MALDI ion source is shown plotted against the mass to charge ratio of ions in FIG. 3. From FIG. 3 it can be seen that ions having, for example, a mass to charge ratio of 200 are fragmented in an optimal manner when they possess an energy of approximately 10 eV before colliding with collision gas molecules whereas singly charged ions having a mass to charge ratio of 2000 are optimally fragmented when they possess an energy of approximately 100 eV before colliding with collision gas molecules.

Figure 4:
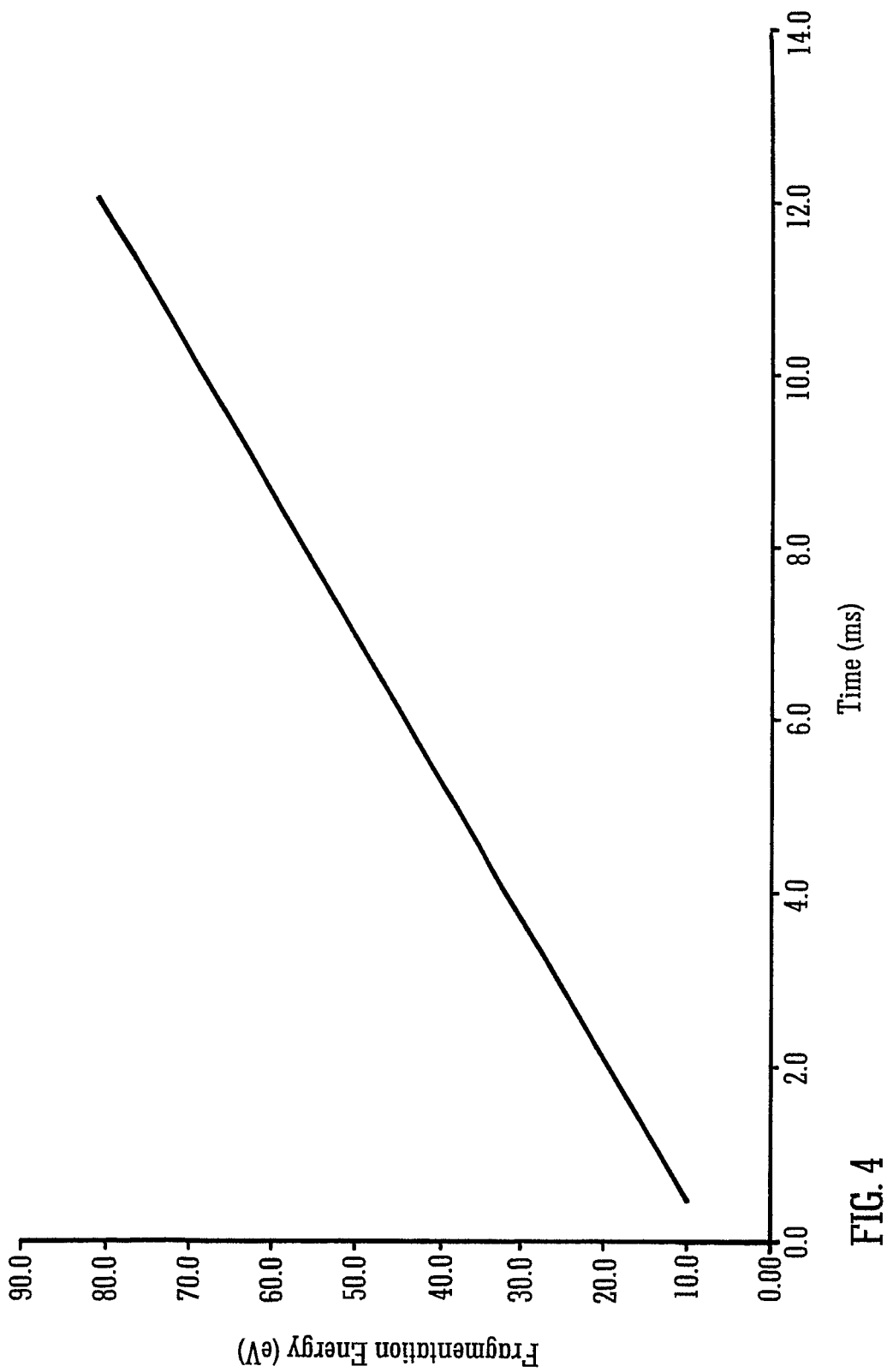
FIG. 4 shows a plot of the optimum energy for fragmentation which ions should possess against the time taken for singly charged ions to drift through an ion mobility spectrometer or separator according to the preferred embodiment.

The data and relationships shown in FIGS. 2 and 3 can be used to calculate the optimal energy which ions emerging from the ion mobility spectrometer or separator 6 and about to enter the fragmentation, collision or reaction device 8 should be arranged to possess as a function of time in order to optimise the fragmentation of ions. The optimum fragmentation energy varies as function of mass to charge ratio of the ions. Since the mass to charge ratio of ions emerging from the ion mobility spectrometer or separator 6 at any point in time will be generally known, then the relationship between the optimum fragmentation energy and the time since a packet or pulse of ions is admitted into the ion mobility spectrometer or separator 6 can be determined. FIG. 4 shows a graph of how the fragmentation energy of ions should preferably be arranged to vary as a function of time according to a preferred embodiment.

According to the preferred embodiment as parent or precursor ions emerge from the ion mobility spectrometer or separator 6 and subsequently pass to the fragmentation, collision or reaction device 8 they are preferably accelerated through a potential difference such that the ions will then be fragmented within the fragmentation, collision or reaction device 8 in a substantially optimal manner. Resulting fragment or daughter ions created within the fragmentation, collision or reaction device 8 are then preferably arranged to exit the fragmentation device 8. The fragment or daughter ions may be urged to leave the fragmentation, collision or reaction device 8 by the application of a constant or time varying electric field which is applied along the length of the fragmentation, collision or reaction device 8. The fragment or daughter ions which emerge from the fragmentation, collision or reaction device 8 then preferably pass through the further transfer optic 9 or ion guide and are then preferably mass analysed by, for example, an orthogonal acceleration Time of Flight mass analyser 10. However, according to other embodiments the ions may be mass analysed by alternative forms of mass analyser.

The preferred embodiment facilitates efficient and optimal fragmentation of parent or precursor ions over substantially the entire mass to charge ratio range of interest. The preferred embodiment therefore results in a significantly increased or improved fragment ion sensitivity and substantially reduced precursor or parent ion crossover into fragment ion mass spectra. The preferred embodiment enables fragment ion mass spectra to be produced wherein substantially all the ions observed in the fragment ion mass spectra are actually fragment ions. This represents an important improvement over conventional approaches wherein parent or precursor ions may still be observed in what is supposed to be a fragment ion mass spectrum due to the fact that some parent or precursor ions are not fragmented in an optimal manner.

Although a MALDI ion source may be used, other ion sources may be used including, for example, an Atmospheric Pressure Ionisation ("API") ion source and in particular an Electrospray ionisation ion source are equally preferred. Most conventional Atmospheric Pressure Ionisation ion sources and Electrospray ion sources in particular differ from MALDI ion sources in that they tend to generate parent or precursor ions which are multiply charged rather than singly charged. However, the preferred embodiment is equally applicable to arrangements wherein multiply charged ions are produced or generated by the ion source or wherein multiply charged ions are passed to the ion mobility spectrometer or separator 6.

According to the preferred embodiment if multiply charged ions are generated by the ion source 1, transmitted to the ion mobility spectrometer or separator 6 and then passed to the fragmentation, collision or reaction device 8 then the collision energy of the multiply charged ions may preferably be increased in proportion to the number of charges relative to singly charged ions being accelerated through the same potential difference. For example, considering ions having the same mass to charge ratio, then if the optimum collision energy of a singly charged ion is 10 eV then the collision energy for a doubly charged ion is set at 20 eV and the collision energy for a triply charged ion is set at 30 eV etc.

As will be appreciated by those skilled in the art, the exact correspondence between optimal fragmentation energy as a function of drift time through the ion mobility spectrometer or separator 6 will vary slightly for multiply charged ions but the general principle of operation of the preferred embodiment of progressively increasing the energy of ions emerging from the ion mobility spectrometer or separator 6 as a function of time will remain substantially the same.

An exception to the preferred embodiment (wherein the kinetic energy of ions emerging from the ion mobility spectrometer or separator is preferably increased with time) is contemplated wherein the mass spectrometer switches from optimising the fragmentation of doubly (or multiply) charged ions to optimising the fragmentation of singly charged ions. Doubly (or multiply) charged ions having a certain mass to charge ratio will exit the ion mobility spectrometer or separator 6 before singly charged ions having the same mass to charge ratio. Doubly charged ions may, for example, be arranged to obtain a kinetic energy of 20 eV. When the mass spectrometer then switches to optimise the fragmentation of singly charged ions having the same mass to charge ratio, the singly charged ions may be arranged to obtain a kinetic energy of 10 eV.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer comprising:
   an ion mobility spectrometer comprising a drift tube, said ion mobility spectrometer being configured to temporally separate ions according to their ion mobility to form temporally separated ions;
   one or more ion-optical devices and an ion trapping device arranged upstream of said ion mobility spectrometer;
   a first fragmentation, collision or reaction device that produces product ions from parent ions and is arranged downstream of said ion mobility spectrometer; and
   a voltage source configured in a first mode of operation to progressively vary or scan or step a potential difference between said ion mobility spectrometer and said first fragmentation, collision or reaction device based on the time at which ions are admitted into said ion mobility spectrometer such that the temporally separated ions pass through a substantially optimum potential difference for fragmentation as the temporally separated ions enter said first fragmentation, collision or reaction device, whilst maintaining each of said one or more ion-optical devices and the ion trapping device at a respective substantially constant potential.

2. A mass spectrometer as claimed in claim 1, wherein said one or more ion-optical devices includes a pulsed or continuous ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

3. A mass spectrometer as claimed in claim 2, wherein said one or more ion-optical devices further includes an ion guide comprising:
   (i) a multipole rod set or a segmented multipole rod set ion guide, wherein said multipole rod set or said segmented multipole rod set ion guide comprises a quadrupole rod set ion guide, a hexapole rod set ion guide, an octapole rod set ion guide or a rod set ion guide comprising more than eight rods;
   (ii) an ion tunnel or ion funnel ion guide, wherein said ion tunnel or ion funnel ion guide comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of said electrodes have apertures which are of substantially the same size or area or which have apertures which become progressively larger or smaller in size or in area, wherein at least 5%, 10%, 15%, 20%, 25%, 30%, 35%, 40%, 45%, 50%, 55%, 60%, 65%, 70%, 75%, 80%, 85%, 90%, 95% or 100% of said electrodes have internal diameters or dimensions selected from the group consisting of: (i) $\leq 1.0$ mm; (ii) $\leq 2.0$ mm; (iii) $\leq 3.0$ mm; (iv) $\leq 4.0$ mm; (v) $\leq 5.0$ mm; (vi) $\leq 6.0$ mm; (vii) $\leq 7.0$ mm; (viii) $\leq 8.0$ mm; (ix) $\leq 9.0$ mm; (x) $\leq 10.0$ mm; and (xi) $> 10.0$ mm; or (iii) a stack or array of planar, plate or mesh electrodes forming an ion guide, wherein said stack or array of planar, plate or mesh electrodes comprises a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of said planar, plate or mesh electrodes are arranged generally in the plane in which ions travel in use, said mass spectrometer further comprising an AC or RF voltage source for supplying said plurality of planar, plate or mesh electrodes with an AC or RF voltage and wherein adjacent planar, plate or mesh electrodes are supplied with opposite phases of said AC or RF voltage;

said mass spectrometer further comprising a transient DC voltage source configured in a second mode of operation to apply one or more transient DC voltages or potentials or one or more transient DC voltage or potential waveforms to electrodes forming said ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion guide or AC or RF voltage source configured to apply two or more phase-shifted AC or RF voltages to electrodes forming said ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion guide.

4. A mass spectrometer as claimed in claim 3, wherein:
(i) said ion guide has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm; or
(ii) said ion guide further comprises an AC or RF voltage source configured to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of said plurality of electrodes of said ion guide in order to confine ions radially within said ion guide, wherein said AC or RF voltage source is configured to supply an AC or RF voltage to said plurality of electrodes of said ion guide having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak or wherein said AC or RF voltage source is configured to supply an AC or RF voltage to said plurality of electrodes of said ion guide having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz; or
(iii) said mass spectrometer further comprises a device for maintaining at least a portion of said ion guide at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) 0.0001-0.1 mbar; and (viii) 0.001-0.01 mbar.

5. A mass spectrometer as claimed in claim 3, wherein said one or more ion-optical devices further includes a mass filter/analyser comprising a quadrupole rod set mass filter or analyser, a Time of Flight mass filter or mass analyser, a Wein filter or a magnetic sector mass filter or mass analyser.

6. A mass spectrometer as claimed in claim 5, wherein said one or more ion-optical devices further includes a second fragmentation, collision or reaction device arranged upstream of said ion mobility spectrometer; or wherein said first fragmentation, collision or reaction device or said second fragmentation, collision or reaction device comprises:
(i) a collision or fragmentation cell arranged to fragment ions by Collisional Induced Dissociation ("CID"); or
(ii) a multipole rod set; or
(iii) a quadrupole, hexapole, octapole or higher order rod set; or
(iv) a plurality of electrodes, at least 10, 20, 30, 40, 50, 60, 70, 80, 90 or 100 electrodes, wherein:
(a) at least 5%, 10%, 15%, 20%, 25%, 30%, 35%, 40%, 45%, 50%, 55%, 60%, 65%, 70%, 75%, 80%, 85%, 90%, 95% or 100% of said electrodes of said first fragmentation, collision or reaction device or said second fragmentation, collision or reaction device have apertures through which ions are transmitted in use; or
(b) at least 5%, 10%, 15%, 20%, 25%, 30%, 35%, 40%, 45%, 50%, 55%, 60%, 65%, 70%, 75%, 80%, 85%, 90%, 95% or 100% of said electrodes of said first fragmentation, collision or reaction device or said second fragmentation, collision or reaction device have apertures which are of substantially the same size or area; or
I at least 5%, 10%, 20%, 30%, 40%, 50%, 60%, 70%, 80%, 90%, 95% or 100% of said electrodes of said first fragmentation, collision or reaction device or said second fragmentation, collision or reaction device have apertures which become progressively larger or smaller in size or in area in a direction along the axis of said fragmentation, collision or reaction device; or
(d) at least 5%, 10%, 20%, 30%, 40%, 50%, 60%, 70%, 80%, 90%, 95% or 100% of said electrodes of said first fragmentation, collision or reaction device or said second fragmentation, collision or reaction device have apertures having internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm; or
(v) a plurality of plate or mesh electrodes and wherein at least some of said plate or mesh electrodes are arranged generally in the plane in which ions travel in use, or wherein at least 50%, 55%, 60%, 65%, 70%, 75%, 80%, 85%, 90%, 95% or 100% of said plate or mesh electrodes are arranged generally in the plane in which ions travel in use, wherein said first fragmentation, collision or reaction device or said second fragmentation, collision or reaction device comprises at least 2, 3, 4, 5, 6, 7, 8, 9, 10, 11, 12, 13, 14, 15, 16, 17, 18, 19, 20 or >20 plate or mesh electrodes or wherein said plate or mesh electrodes are supplied with an AC or RF voltage and adjacent plate or mesh electrodes are supplied with opposite phases of said AC or RF voltage; or
(vi) a plurality of axial segments, at least 5, 10, 15, 20, 25, 30, 35, 40, 45, 50, 55, 60, 65, 70, 75, 80, 85, 90, 95 or 100 axial segments.

7. A mass spectrometer as claimed in claim 6, further comprising:
(i) a DC voltage source for maintaining a substantially constant DC voltage gradient along at least a portion of an axial length of said first fragmentation, collision or reaction device or said second fragmentation, collision or reaction device, wherein said DC voltage source is configured to maintain a substantially constant DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of said first fragmentation, collision or reaction device or said second fragmentation, collision or reaction device; or
(ii) a transient DC voltage source configured to apply one or more transient DC voltages or potentials or one or more transient DC voltage or potential waveforms to electrodes forming said first fragmentation, collision or reaction device or said second fragmentation, collision or reaction device in order to urge at least some ions along at least a portion of the axial length of said first fragmentation, collision or reaction device or said second fragmentation, collision or reaction device, wherein said transient DC voltage source is configured to apply one or more transient DC voltages or potentials or one or more transient DC voltage or potential waveforms to electrodes along at least 5%, 10%, 15%, 20%, 25%, 30%, 35%, 40%, 45%, 50%, 55%, 60%, 65%, 70%, 75%, 80%, 85%, 90%, 95% or 100% of the axial length of said first fragmentation, collision or reaction device or said second fragmentation, collision or reaction device; or
(iii) an AC or RF voltage source configured to apply one or more AC or RF voltages to electrodes forming said first fragmentation, collision or reaction device or said second fragmentation, collision or reaction device in order to urge at least some ions along at least a portion of the axial length of said first fragmentation, collision or reaction device or said second fragmentation, collision or reaction device, wherein said AC or RF voltage source is configured to apply one or more AC or RF voltages to electrodes along at least 5%, 10%, 15%, 20%, 25%, 30%, 35%, 40%, 45%, 50%, 55%, 60%, 65%, 70%, 75%, 80%, 85%, 90%, 95% or 100% of the axial length of said first fragmentation, collision or reaction device or said second fragmentation, collision or reaction device.

8. A mass spectrometer as claimed in claim 6, wherein said first fragmentation, collision or reaction device or said second fragmentation, collision or reaction device comprises a plurality of electrodes, said mass spectrometer further comprising an AC or RF voltage source configured to apply an AC or RF voltage to at least 1%, 5%, 10%, 20%, 30%, 40%, 50%, 60%, 70%, 80%, 90%, 95% or 100% of said plurality of electrodes of said first fragmentation, collision or reaction device or said second fragmentation, collision or reaction device, or wherein said AC or RF voltage source is configured to supply an AC or RF voltage to said plurality of electrodes of said first fragmentation, collision or reaction device or said second fragmentation, collision or reaction device having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak, wherein said AC or RF voltage source is configured to supply an AC or RF voltage to said plurality of electrodes of said first fragmentation, collision or reaction device or said second fragmentation, collision or reaction device having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

9. A mass spectrometer as claimed in claim 1, wherein the first fragmentation, collision or reaction device or said second fragmentation, collision or reaction device comprise a collision, fragmentation or reaction device selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions,
said mass spectrometer further comprising a device for maintaining at least a portion of said first fragmentation, collision or reaction device or said second fragmentation, collision or reaction device at a pressure selected from the group consisting of: (i) $>1.0 \times 10^{-3}$ mbar; (ii) $>1.0 \times 10^{-2}$ mbar; (iii) $>1.0 \times 10^{-1}$ mbar; (iv) >1 mbar; (v) >10 mbar; (vi) >100 mbar; (vii) $>5.0 \times 10^{-3}$ mbar; (viii) $>5.0 \times 10^{-2}$ mbar; (ix) $10^{-3}$-$10^{-2}$ mbar; and (x) $10^{-4}$-$10^{-1}$ mbar; or further comprising a device for trapping ions within said first fragmentation, collision or reaction device or said second fragmentation, collision or reaction device in a mode of operation.

10. A mass spectrometer as claimed in claim 6, further comprising a control system configured to switch or repeatedly switch said first fragmentation, collision or reaction device or said second fragmentation, collision or reaction device between a first mode of operation wherein ions are substantially fragmented and a second mode of operation wherein substantially less or no ions are fragmented,
  wherein in said first mode of operation temporally separated ions exiting said ion mobility spectrometer are accelerated through a potential difference selected from the group consisting of: (i) ≥10 V; (ii) ≥20 V; (iii) ≥30 V; (iv) ≥40 V; (v) ≥50 V; (vi) ≥60 V; (vii) ≥70 V; (viii) ≥80 V; (ix) ≥90 V; and (x) ≥100 V, or
  wherein in said second mode of operation temporally separated ions exiting said ion mobility spectrometer are accelerated through a potential difference selected from the group consisting of: (i) ≤20 V; (ii) ≤15 V; (iii) ≤10 V; (iv) ≤5V; and (v) ≤1V, or
  wherein said control system is configured to switch said first fragmentation, collision or reaction device or said second fragmentation, collision or reaction device between said first mode of operation and said second mode of operation at least once every 1 ms, 5 ms, 10 ms, 15 ms, 20 ms, 25 ms, 30 ms, 35 ms, 40 ms, 45 ms, 50 ms, 55 ms, 60 ms, 65 ms, 70 ms, 75 ms, 80 ms, 85 ms, 90 ms, 95 ms, 100 ms, 200 ms, 300 ms, 400 ms, 500 ms, 600 ms, 700 ms, 800 ms, 900 ms, 1 s, 2 s, 3 s, 4 s, 5 s, 6 s, 7 s, 8 s, 9 s or 10 s.

11. A mass spectrometer as claimed in claim 1, wherein said ion trapping device comprises:
  (i) a multipole rod set or a segmented multipole rod set, wherein said multipole rod set or said segmented multipole rod set comprises a quadrupole rod set, a hexapole rod set, an octapole rod set or a rod set comprising more than eight rods;
  (ii) an ion tunnel or ion funnel, wherein said ion tunnel or ion funnel comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of said electrodes have apertures which are of substantially the same size or area or which have apertures which become progressively larger or smaller in size or in area, or
  (iii) a stack or array of planar, plate or mesh electrodes, wherein said stack or array of planar, plate or mesh electrodes comprises a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of said planar, plate or mesh electrodes are arranged generally in the plane in which ions travel in use, and further comprising a first AC or RF voltage source for supplying said plurality of planar, plate or mesh electrodes with an AC or RF voltage and wherein adjacent planar, plate or mesh electrodes are supplied with opposite phases of said AC or RF voltage;
  wherein said ion trapping device further comprises a second AC or RF voltage source configured to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of said plurality of electrodes of said ion trapping device in order to confine ions radially within said ion trapping device, and wherein said second AC or RF voltage source is configured to supply an AC or RF voltage to said plurality of electrodes of said ion trapping device having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak, or wherein said second AC or RF voltage source is configured to supply an AC or RF voltage to said plurality of electrodes of said ion trapping device having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

12. A mass spectrometer as claimed in claim 1, wherein said voltage source is configured to vary or alter or scan or step a potential difference through which temporally separated ions pass as temporally separated ions pass from said ion mobility spectrometer to said first fragmentation, collision or reaction device, or
  wherein said voltage source is configured to accelerate first temporally separated ions emerging from said ion mobility spectrometer at a time $t_1$ through a first potential difference $V_1$ and to accelerate second different temporally separated ions emerging from said ion mobility spectrometer at a second later time $t_2$ through a second different potential difference $V_2$, wherein $V_2 > V_1$; or
  wherein said voltage source is configured to progressively increase the potential difference through which temporally separated ions pass as they are transmitted from said ion mobility spectrometer to said first fragmentation, collision or reaction device, wherein $V_2 < V_1$, or
  wherein said voltage source is configured to accelerate or decelerate temporally separated ions into said first fragmentation, collision or reaction device.

13. A mass spectrometer as claimed in claim 1, wherein said ion mobility spectrometer comprises:
  (i) a gas phase electrophoresis device; or
  (ii) a drift tube and one or more electrodes for maintaining an axial DC voltage gradient along at least a portion of said drift tube, further comprising a second voltage source for maintaining an axial DC voltage gradient along at least a portion of said drift tube; or
  (iii) one or more multipole rod sets, one or more quadrupole, hexapole, octapole or higher order rod sets, wherein said one or more multipole rod sets are axially segmented or comprise a plurality of axial segments; or
  (iv) a plurality of electrodes, at least 10, 20, 30, 40, 50, 60, 70, 80, 90 or 100 electrodes, wherein:
    (a) at least 5%, 10%, 15%, 20%, 25%, 30%, 35%, 40%, 45%, 50%, 55%, 60%, 65%, 70%, 75%, 80%, 85%, 90%, 95% or 100% of said electrodes of said ion mobility spectrometer have apertures through which ions are transmitted in use; or (b) at least 5%, 10%, 15%, 20%, 25%, 30%, 35%, 40%, 45%, 50%, 55%, 60%, 65%, 70%, 75%, 80%, 85%, 90%, 95% or 100% of said electrodes of said ion mobility spectrometer have apertures which are of substantially the same size or area; or I at least 5%, 10%, 15%, 20%, 25%, 30%, 35%, 40%, 45%, 50%, 55%, 60%, 65%, 70%, 75%, 80%, 85%, 90%, 95% or 100% of said electrodes of said ion mobility spectrometer have apertures which become progressively larger or smaller in size or in area in a direction along the axis of said ion guide or ion trapping device; or (d) at least 5%, 10%, 15%, 20%, 25%, 30%, 35%, 40%, 45%, 50%, 55%, 60%, 65%, 70%, 75%, 80%, 85%, 90%, 95% or 100% of said electrodes of said ion mobility spectrometer have apertures having internal diameters or dimensions selected from the group consisting of: (i) $\leq 1.0$ mm; (ii) $\leq 2.0$ mm; (iii) $\leq 3.0$ mm; (iv) $\leq 4.0$ mm; (v) $\leq 5.0$ mm; (vi) $\leq 6.0$ mm; (vii) $\leq 7.0$ mm; (viii) $\leq 8.0$ mm; (ix) $\leq 9.0$ mm; (x) $\leq 10.0$ mm; and (xi) $>10.0$ mm; or (v) a plurality of plate or mesh electrodes and wherein at least some of said plate or mesh electrodes are arranged generally in the plane in which ions travel in use or wherein at least 50%, 55%, 60%, 65%, 70%, 75%, 80%, 85%, 90%, 95% or 100% of said plate or mesh electrodes are arranged generally in the plane in which ions travel in use, wherein said ion mobility spectrometer comprises at least 2, 3, 4, 5, 6, 7, 8, 9, 10, 11, 12, 13, 14, 15, 16, 17, 18, 19, 20 or >20 plate or mesh electrodes, or wherein said plate or mesh electrodes are supplied with an AC or RF voltage and adjacent plate or mesh electrodes are supplied with opposite phases of said AC or RF voltage; or (vi) a plurality of axial segments, at least 5, 10, 15, 20, 25, 30, 35, 40, 45, 50, 55, 60, 65, 70, 75, 80, 85, 90, 95 or 100 axial segments;

said mass spectrometer further comprising:

(vii) a DC voltage source for maintaining a substantially constant DC voltage gradient along at least a portion of the axial length of said ion mobility spectrometer or (viii) a transient DC voltage source configured to apply one or more transient DC voltages or potentials or one or more transient DC voltage or potential waveforms to electrodes forming said ion mobility spectrometer in order to urge at least some ions along at least a portion of the axial length of said ion mobility spectrometer; or (ix) an AC or RF voltage source configured to apply one or more AC or RF voltages to electrodes forming said ion mobility spectrometer in order to urge at least some ions along at least a portion of the axial length of said ion mobility spectrometer.

14. A mass spectrometer as claimed in claim 6, further comprising a mass analyser arranged downstream of said first fragmentation, collision or reaction device or said second fragmentation, collision or reaction device, wherein said mass analyser is selected from the group consisting of: (i) a Fourier Transform ("FT") mass analyser; (ii) a Fourier Transform Ion Cyclotron Resonance ("FTICR") mass analyser; (iii) a Time of Flight ("TOF") mass analyser; (iv) an orthogonal acceleration Time of Flight ("oaTOF") mass analyser; (v) an axial acceleration Time of Flight mass analyser; (vi) a magnetic sector mass spectrometer; (vii) a Paul or 3D quadrupole mass analyser; (viii) a 2D or linear quadrupole mass analyser; (ix) a Penning trap mass analyser; (x) an ion trap mass analyser; (xi) a Fourier Transform orbitrap; (xii) an electrostatic Ion Cyclotron Resonance mass spectrometer; (xiii) an electrostatic Fourier Transform mass spectrometer; and (xiv) a quadrupole mass analyser.

15. A method of mass spectrometry conducted with an ion mobility spectrometer comprising a drift tube, one or more ion-optical devices upstream of said ion mobility spectrometer, an ion trapping device upstream of said ion mobility spectrometer, and a first fragmentation, collision or reaction device that produces product ions from parent ions and is arranged downstream of said ion mobility spectrometer, said method comprising:

temporally separating ions according to their ion mobility in said ion mobility spectrometer to form temporally separated ions; and progressively varying or scanning or stepping the potential difference between said ion mobility spectrometer and said first fragmentation, collision or reaction device based on the time at which ions are admitted into said ion mobility spectrometer such that the temporally separated ions pass through a substantially optimum potential difference for fragmentation as the temporally separated ions enter said first fragmentation, collision or reaction device, whilst maintaining each of said one or more ion-optical devices and said ion trapping device at a respective substantially constant potential.

16. The method of mass spectrometry according to claim 15, wherein progressively varying or scanning or stepping the potential difference between said ion mobility spectrometer and said first fragmentation, collision or reaction device includes varying or scanning or stepping in time the potential difference.

17. A mass spectrometer as claimed in claim 1, wherein said voltage source is configured in the first mode of operation to progressively vary or scan or step in time the potential difference between said ion mobility spectrometer and said first fragmentation, collision or reaction device.

* * * * *